Figure 1:
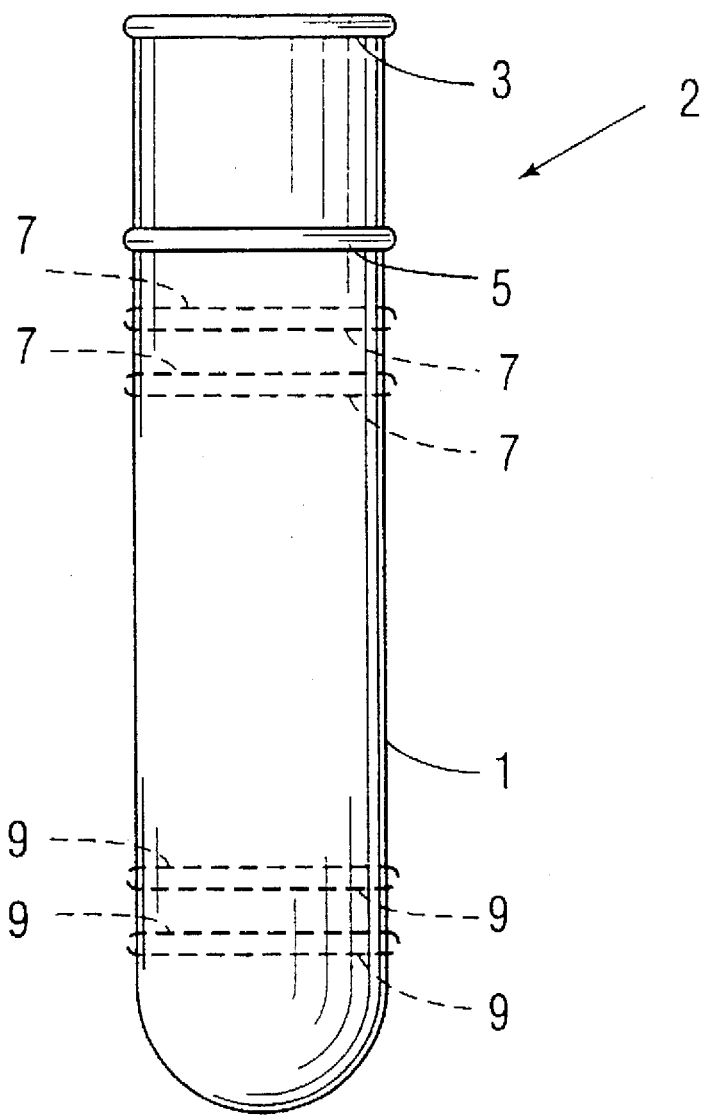

United States Patent [19]
Strauss et al.

[11] Patent Number: 5,715,839
[45] Date of Patent: Feb. 10, 1998

[54] MULTIPLE RING CONDOM

[75] Inventors: Steven R. Strauss, Hillsdale; Frederick P. Sisbarro, Wayne, both of N.J.

[73] Assignee: Carter-Wallace, Inc., New York, N.Y.

[21] Appl. No.: 821,382

[22] Filed: Mar. 20, 1997

Related U.S. Application Data

[63] Continuation of Ser. No. 598,056, Feb. 7, 1996, abandoned, which is a continuation of Ser. No. 279,573, Jul. 22, 1994, abandoned.

[51] Int. Cl.$^6$ ................................................ A61F 6/02
[52] U.S. Cl. ........................................ 128/842; 128/844
[58] Field of Search ............................. 128/842, 844, 128/918; 604/347–353

[56] References Cited

U.S. PATENT DOCUMENTS

| | | | |
|---|---|---|---|
| 3,130,721 | 4/1964 | Young | 128/844 |
| 4,798,600 | 1/1989 | Meadows | 128/844 |
| 5,370,130 | 12/1994 | Hess | 128/844 |
| 5,425,379 | 6/1995 | Broad | 128/842 |
| 5,467,781 | 11/1995 | Kato | 128/844 |
| 5,490,519 | 2/1996 | Hessel | 128/844 |
| 5,579,784 | 12/1996 | Harari | 128/844 |

*Primary Examiner*—Michael A. Brown
*Attorney, Agent, or Firm*—Watov & Kipnes, P.C.

[57] ABSTRACT

Multiple ringed condoms providing improved user protection and safety from leakage and slippage are provided by adding one or more additional rings above the conventional base ring at the opening of the condom.

4 Claims, 1 Drawing Sheet

MULTIPLE RING CONDOM

This application is a continuation of Ser. No. 08/598,056 filed Feb. 7, 1996 now abandoned, which is a continuation of Ser. No. 08/279,573 filed July 22, 1994 now abandoned.

This invention relates to novel condoms made of natural rubber latex, fine animal skins, polyurethane and other synthetic materials. More particularly, this invention is concerned with reducing the slippage and leakage of such condoms during use. Specifically, this invention is concerned with improving the properties of dipped vulcanized natural rubber latex, natural skin and synthetic condoms. More specifically, this invention is concerned with reducing slippage and leakage of condoms during use without increasing the thickness of the condom and consequent loss of sensitivity to the user.

There has developed around natural rubber latex a substantial industry for producing such articles as condoms, rubber gloves, surgical supplies, balloons, bathing caps and countless other articles. The articles are generally produced by dipping glass, porcelain or metal forms into natural rubber latex baths and subsequently coagulating and curing the thin film of latex which adheres to the form. Thicker films are obtained by repeating the dipping, coagulating and curing operations as desired. The films are then usually stripped from the molds and optionally may be further cured at elevated temperatures.

Natural rubber lattices are particularly useful in dipping operations, since, unlike synthetic rubber lattices such as chloroprene polymers (neoprene rubber), butadiene-styrene copolymers (Buna S rubber) or butadiene-acrylonitrile copolymers (Buna N rubber), natural rubber latex in its membranous form possesses a very high degree of wet film strength.

As used herein, the term "natural rubber" refers to elastomeric substances obtained from trees or plants such as the quayule and the hevea rubber trees usually by directly tapping the trees by means of cuts into the bark of the tree. The fluid which flows from the tree is not a part of the tree's sap but is natural rubber latex. The latex is made up of individual particles varying in size from between about 0.005 and 2.5 microns. Chemically the particles are stereoregular polymers of cis-1,4 polyisoprene carrying a negative charge with an isoelectric point in about the 4–5 pH range.

Natural rubber latex is subject to putrification and coagulation within a few hours of collection unless a chemical stabilizer and/or preservative is added to the latex. As a practical matter, stabilizers and preservatives such as ammonia or combinations of ammonia and blends of secondary preservatives such as tetramethylthiuram disulfide, which also functions as a vulcanizer and accelerator, and zinc oxide are added directly to containers used in the collection of the latex.

The rubber content of the natural rubber lattices as collected is usually between about 30 to 40 percent by weight. Generally, the lattices are concentrated by one of several well established methods, i.e., heat concentrating, centrifuging or creaming to produce lattices having a rubber content of from about 60 to 75 percent for commercial use. The lattices employed in the present invention have a rubber content ranging from about 35% to about 65% by weight.

In addition, as is well known in the art, reinforcing agents such as fumed silica and other materials, commonly known as "rubber chemicals", that impart particularly desired properties to the finished dipped goods may be added to the latex, i.e., curing, cross-linking or vulcanizing agents such as sulphur, vulcanization accelerators and activators, including metal oxides and hydroxides, i.e., zinc, calcium, sodium and organic accelerators such as the dithio carbamates, xanthates, thiourea, mercapto compounds, etc., antioxidants and other antidegradants in amounts that vary depending on characteristics of the latex, solids content and properties desired.

Preferably, the rubber chemicals employed, if not water soluble, are of a particle size approximately equal to the rubber particle size in the latex. Moreover, water insoluble materials should be emulsified or dispersed in water prior to blending or mixing into the latex. The compounding of the rubber chemicals and latex usually takes place under ambient conditions, preferably at about 75° F. after which the mixture is aged or stored for about twenty four hours. The amount of hydrophilic fumed silica reinforcing agent subsequently added to the mixture is from about 0.5 to about 15 parts per 100 parts rubber in the natural rubber latex. Preferably about 5 parts hydrophilic fumed silica per 100 parts by weight of natural rubber in the latex.

Recently, there has been an increased interest in the production of condoms from natural rubber latex formulations as well as from synthetic elastomeric polymers and an effort has been undertaken by the industry to improve the properties of such dipped latex articles. Moreover, numerous attempts have been made to design and improve condoms in order to provide greater protection against conception and/or against the transmission of sexually transmitted disease.

Normally the condom is made of strong, fine rubber, or some type of fine animal skin or a synthetic membrane such as polyurethane. Of necessity, in order to provide an acceptable level of tactile stimulation to the wearer, the condom must be quite thin. In general, it is elastically fitted to the male organ and during coitus remains stretched and taut. This stretched, taut condition can increase the hazard of the condom being torn or bursting during use and can also compromise the integrity of the condom insofar as leakage and slippage are concerned.

In accordance with the present invention, methods have now been found for improving the user protection and safety associated with condoms by adding one or more additional rings below the conventional ring at the opening of the condom whereby the incidence of slippage and leakage of the condom during use is substantially reduced, i.e. when following ejaculation the penis becomes flaccid, a possibility of leakage of seminal fluid and slippage of the condom occurs. While the distance between rings on the condom is not critical, i.e. enhanced clitoral stimulation is obtained by placing the additional ring or rings closer to the closed end of the condom, a distance of from about one-quarter inch to about four inches between rings has been found to be suitable.

The traditional methods of manufacturing a contraceptive, prophylactic or condom involve the so-called straight dipping or dip and dry techniques wherein a phallic shaped mandrel, normally of ceramic, metal or glass composition, of predetermined size is, optionally coated with a coagulating agent, and dipped into a bath containing natural rubber latex or a solution of synthetic material such as polyurethane. The mandrel when dipped may be stationary or rotating about its longitudinal axis. Optionally, a circumferential groove in the mandrel may be located towards the upper open end of the mandrel. The mandrel, when immersed in the latex bath, is immersed to a depth sufficient to yield the finished condom of desired length plus an additional distance to allow for rolling the sheath on itself for several turns in order to form a latex ring at the open end of the condom or optionally to a depth coincident with the upper edge of the circumferential groove which would then form the latex ring. After a predetermined period of time the mandrel, covered with a coating of latex which conforms to the mandrel's shape, optionally including the circumferential ring, is withdrawn. In accordance with the preferred embodiment of the present invention, the mandrel containing the condom with the circumferential ring is again dipped into the latex bath to a depth sufficient to yield the finished condom of desired length plus an additional distance to allow for formation of a second ring at the open end of the condom in the manner set forth above. The latex coating is allowed to dry or is cured at elevated temperatures to form a latex sheath containing two thickened rings of latex formed at its upper open end. Alternatively, the ring or beading may be formed by rolling the sheath on itself for several turns, then curing the sheath and applying an anti-tack agent. Depending on the desired thickness of the latex sheath, and the number of additional rings desired, the dipping and curing operation may be repeated one or more additional times.

Optionally, upon completion of the final cure, the formed latex sheath may be coated with an anti-tack material such as talc, microporous solid particles, lubricants, slip agents, spermicides, deodorants, etc., prior to removal from the mandrel.

After completion of the dipping, ring-forming, curing and optional coating steps, the sheath is removed from the mandrel by starting from the upper portion of the latex sheath and rolling the sheath off the mandrel surface around the thickened latex rings or beads to form a cup-shaped elastic ring of predetermined size and circumference. The result is several layers of latex being rolled around the thickened latex ring formed at the top, open end, of the sheath forming a cup within the circumference of the ring. In this form, the prophylactic sheath is easily mountable for use during sexual intercourse. At this point, additional lubricants, spermicides, bactericides, etc., may also be added to the cup-shaped latex sheath.

Certain classes of elastomeric polymers may be used to form condoms in lieu of latex, such as polyurethanes which provide a strength and tensile modulus approximately three times those of latex. In addition, unlike natural rubber, polyurethanes are resistant to petroleum based lubricants and have better thermal and oxidative stability than natural rubber.

Polyurethane condoms may be prepared using dip-molding techniques wherein a phallic shaped mandrel is dipped into a polyurethane solution. Cure is achieved by means of heat once the mandrel is raised from the solution with the additional advantage that the use of curing agents, coagulation agents or other means to effect polymer curing may not be required.

The formation of the multiple rings of the present invention can be accomplished with polyurethanes in the same manner as described with respect to latex condoms.

In the case of natural skin condoms, the multiple rings of the present invention, in the form of an elastomeric ring, may be sewn or glued to the condom.

In addition to the standard form of condom, it is also within the scope of the present invention to apply multiple rings to so-called loose or baggy condoms, i.e. wherein the condom sheath is sized such that the closed end is of a flat width substantially greater than the flat width of the open end. The differences in flat width between the closed end and the open end of the condom sheath are achieved through dipping mandrel designs which gradually or sharply taper the larger flat width of the closed end of the condom to the smaller flat width of the open end of the condom.

While in general the rings formed on the condom will have approximately equal inside diameters, rings of equal or different inside diameters are contemplated by the present invention, i.e. the additional rings below the base ring at the opening of the condom can have a smaller inside diameter than that of the base ring which will aid in maintaining penal erection and/or preventing premature ejaculation.

The present invention relative to various aspects thereof is shown in the drawing, in which like items are identified by the same reference designation, wherein FIG. 1 is an elevational view of a condom of one embodiment of the invention.

In FIG. 1, a condom 1 as described above is shown. Circumferential ring 3 is formed about the open end of condom 1. Circumferential ring 5 is located below and parallel to ring 3, preferably from one-quarter inch to four inches below ring 3, as previously indicated. One or more additional rings 7 (shown in phantom) may be included below ring 5 in the upper portion of condom 1. One or more rings 9 may also be formed in the lower portion of condom 1. The mandrel (not shown) used in forming condom 1, as described above, is configured as required for forming a condom 1 with a desired number and orientation or combination of rings 5, 7, and 9, respectively.

For a more complete understanding of the invention by those skilled in the art, the following examples are given by way of illustration.

EXAMPLE 1

Preparation of Latex Dipping Bath—35 Grain Condom

A homogeneous stable latex composition is prepared by stirring 2.0 parts by weight zinc oxide, 0.1 parts by weight potassium hydroxide, 0.1 parts by weight sodium dibutyldithiocarbamate and 0.5 parts by weight dispersed sulfur into ammonia preserved 46% solids content natural rubber latex. Mixing was continued for 12 hours and the mixture stored in drums for twenty-four hours.

Double-ringed condoms (35 grain) were dipped from this latex bath using the dipping, ring-forming and curing procedures as hereinabove set forth.

EXAMPLE 2

Preparation of Latex Dipping Bath—22 Grain Condom

The procedure of example 1 was repeated and the volume of the resulting latex composition was increased by the addition of deionized water with mixing to a latex solids content of 42%.

Double-ringed condoms (22 grain) were dipped from this latex bath.

EXAMPLE 3

Preparation of Silica Reinforced Dipping Bath—35 Grain Condom

The procedure of example 1 was repeated. And, 200 pounds of an aqueous dispersion of silica 17.8 weight % solids content was stabilized with ammonia to a pH of 10.0 One hundred eighty three (183) pounds of the stabilized silica dispersion was blended into the latex mixture and stirred for 2.5 hours.

Thirty five (35) grain silica reinforced double-ringed condoms were prepared from the bath by dipping.

EXAMPLE 4

Preparation of Silica Reinforced Dipping Bath—22 Grain Condom

The procedure of example 3 was repeated and the volume of the resulting silica reinforced latex composition was increased by the addition of deionized water with mixing to a latex solids content of 42%.

Twenty two (22) grain silica reinforced double-ringed condoms were prepared from the bath by dipping.

The foregoing, non-limiting examples are offered primarily for purposes of illustration. It will be readily apparent to those skilled in the art that numerous modifications and variations of the components, dimensions and parameters described above may be made without departing from the spirit and scope of the invention.

The foregoing, non-limiting examples are offered primarily for purposes of illustration. It will be readily apparent to those skilled in the art that numerous modifications and variations of the components, dimensions and parameters described above may be made without departing from the spirit and scope of the invention.

What is claimed is:

1. A method for manufacturing a condom, having a plurality of spaced apart circumferential rings, comprising the steps of:

forming a mandrel configured to have the shape and size of said condom, and to have a desired number of spaced apart circumferential grooves for providing said circumferential rings on said condom;

providing a dipping bath consisting of said resilient material;

dipping said mandrel into said bath to a depth for covering or coating a length of said mandrel equivalent to the length of said condom plus an additional distance to allow for rolling the cured material after dipping onto itself from an open end of said condom for forming a ring of desired thickness at the open end;

withdrawing said mandrel from said bath for a predetermined length of time;

dipping said mandrel back into said bath to a depth sufficient to immerse one or more of said circumferential grooves of said mandrel, and a length of said mandrel equivalent to the length of said condom;

successively repeating said withdrawing and subsequent dipping steps until a desired thickness is obtained for said condom and associated circumferential rings;

withdrawing said mandrel from said bath; and curing said coating of material on said mandrel for completing the formation of said condom.

2. The method of claim 1, wherein said resilient material is selected from the group consisting of rubber latex, and polyurethane.

3. A method for manufacturing a condom, having a plurality of spaced apart circumferential rings, comprising the steps of:

forming a mandrel configured to have the shape and size of said condom;

providing a dipping bath consisting of said resilient material;

dipping said mandrel into said bath to a depth for covering or coating a length of said mandrel equivalent to the length of said condom plus an additional distance to allow for rolling the cured material after dipping onto itself from an open end of said condom for forming a ring of desired thickness at the open end;

withdrawing said mandrel from said bath for a predetermined length of time for curing said material;

rolling the cured said material onto itself from an open end of said condom for forming at least one ring of desired thickness at the open end;

dipping said mandrel back into said bath to a depth sufficient to immerse one or more of said rings of said material, and a length of said mandrel equivalent to the length of said condom;

successively repeating said withdrawing and subsequent rolling, and dipping steps until a desired thickness is obtained for said condom, and a desired number of rings are formed;

withdrawing said mandrel from said bath; and curing said coating of material on said mandrel for completing the formation of said condom.

4. The method of claim 3, wherein said resilient material is selected from the group consisting of rubber latex, and polyurethane.

* * * * *